United States Patent [19]

Akutsu

[11] Patent Number: 5,071,623
[45] Date of Patent: Dec. 10, 1991

[54] URINARY TEST PAPER

[76] Inventor: Hidenobu Akutsu, 29-22, Sakuragaoka-cho, Shibuya-ku, Tokyo, Japan

[21] Appl. No.: 465,707

[22] Filed: Jan. 16, 1990

[30] Foreign Application Priority Data

May 11, 1989 [JP] Japan .................................. 1-116177

[51] Int. Cl.$^5$ ........................................... G01N 33/50
[52] U.S. Cl. ...................................... 422/56; 422/57; 435/805; 436/66
[58] Field of Search ...................... 422/56, 57; 436/66; 435/805

[56] References Cited

U.S. PATENT DOCUMENTS

| | | | |
|---|---|---|---|
| 3,127,28 | 3/1964 | Meyer | 422/56 |
| 3,139,328 | 6/1964 | Jacob | 422/56 |
| 3,598,704 | 8/1971 | Dahlquist | 422/56 |
| 3,912,457 | 10/1975 | Ogawa et al. | 422/56 |
| 4,175,923 | 11/1979 | Friend | 436/66 |
| 4,521,520 | 6/1985 | Jacke | 422/56 |
| 4,578,358 | 3/1986 | Oksman et al. | 436/66 |
| 4,578,359 | 3/1986 | Oksman et al. | 436/66 |
| 4,654,310 | 3/1987 | Ly | 422/56 |
| 4,803,171 | 2/1989 | Baier et al. | 422/56 |

FOREIGN PATENT DOCUMENTS 1018563  1/1966  United Kingdom ................. 436/66

*Primary Examiner*—Robert J. Warden
*Assistant Examiner*—Lyle A. Alexander
*Attorney, Agent, or Firm*—Browdy and Neimark

[57] ABSTRACT

The test paper for urinalysis of the present invention is made up of water-soluble paper which consists of 99–45 weight per cent of carboxymethyl cellulose and 1–55 weight per cent of wood pulp. This water-soluble paper is covered or impregnated with one or more reagents needed for urinalysis in order to form an appropriate shape of spots. The urinary test paper of the present invention can be flushed down a toilet bowl or a urinal in a flush toilet after use thereof.

18 Claims, 3 Drawing Sheets

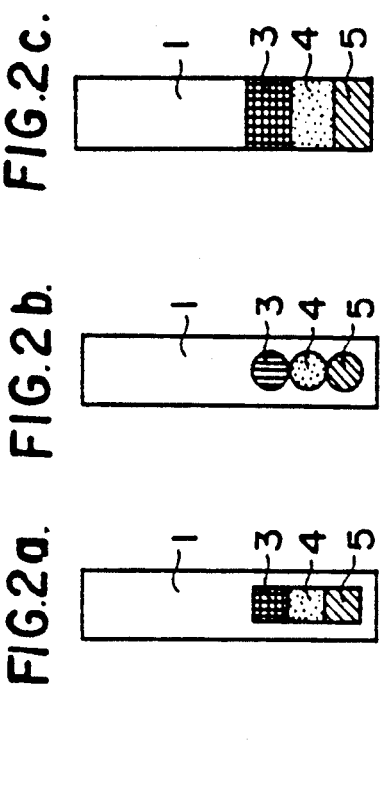
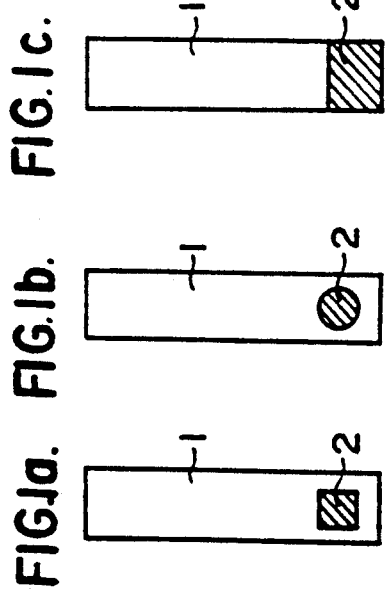
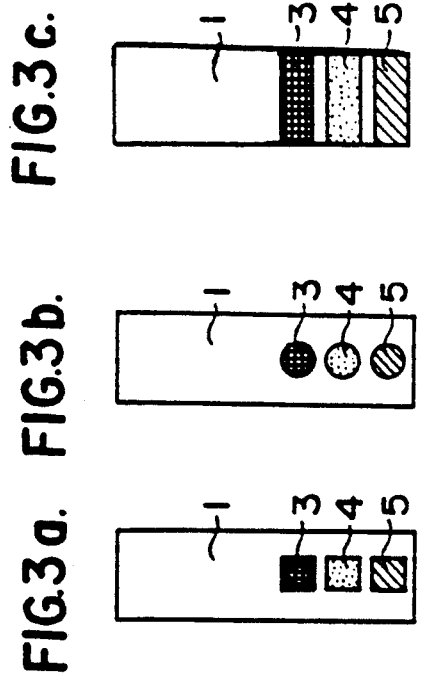

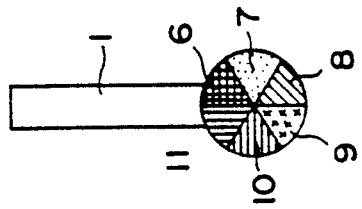
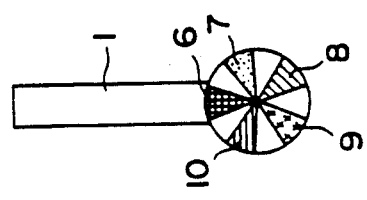
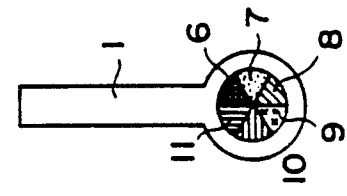
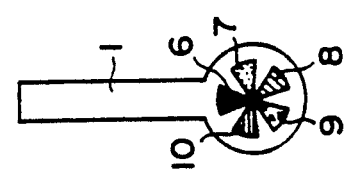
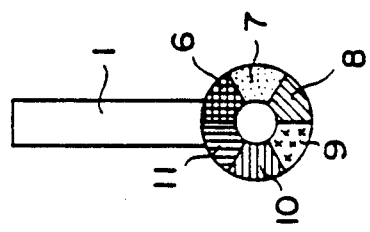
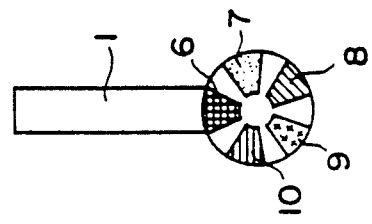
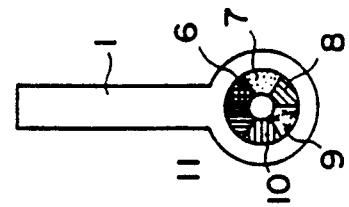
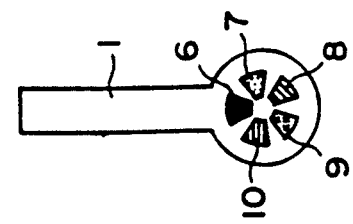

URINARY TEST PAPER

BACKGROUND OF THE INVENTION

The present invention relates to water-soluble test paper for urinalysis whereby signs of various kind of diseases such as diabetes and nephritis can be easily detected beforehand at home.

More particularly, the present invention relates to water-soluble test paper for urinalysis which consists of carboxymethyl cellulose and wood pulp and any place, for example, one end of which is impregnated or covered with one or more reagents.

One of the traditional methods of urinalysis for detection of diabetes and other diseases in hospitals, clinics, etc. is to dip one end of a strip of urinary test paper into a patient's urine taken in a container for examination and thereby diagnose the presence and state of a disease by colorimetric analysis. Filter paper impregnated with one or more test reagents is currently used as urinary test paper for dignosis. A strip of plastic film such as polyester on which a small piece of filter paper impregnated with test reagents is stuck, is also used for urinalysis. After use, these pieces of test paper are disposed of by incineration.

These kinds of urinary test paper are available on the market. One can easily examine his own urine by use of such urinary test papers at home, workplace or another place.

The conventional test paper mentioned above, however, has had the following problem:

Since these kinds of test paper are water-insoluble, they cannot be flushed down a toilet bowl or a urinal in a flush toilet after using them and must therefore be disposed of by incineration instead.

SUMMARY OF THE INVENTION

An object of the present invention is to provide urinary test paper which can be simply used at home at any time and by use of which a sign of a disease such as diabetes can be easily detected even at home.

Another object of the present invention is to provide urinary test paper which can be thrown into a toilet bowl or a urinal in a flush toilet after using it, thereby saving the trouble of disposing of used test paper by incineration.

The urinary test paper of the present invention is produced by the following steps of:

impregnating or covering an appropriate part of water-soluble paper, for example, one end of said paper strip with one or more reagents and thereafter drying the test paper.

BRIEF DESCRIPTION OF THE DRAWINGS

FIG. 1(a-c) shows three types of the urinary test paper strips of the present invention one end of which is impregnated or covered with one reagent.

FIG. 2(a-c) shows three types of the urinary test paper strips of the present invention one end of which is impregnated or covered with three kinds of reagents, the spots of which are placed in contact with each other.

FIG. 3(a-c) shows three types of the urinary test paper strips of the present invention one end of which is impregnated or covered with three kinds of reagents, the spots of which are placed at intervals.

FIGS. 7(a-b), 8(a-b), 9(a-b) and 10(a-b) show a variation of the urinary test paper strips of the present invention one end of which is rounded and impregnated or covered with several kinds of reagents.

DESCRIPTION OF THE PREFERRED EMBODIMENTS

The urinary test papers of the present invention are made of water-soluble paper and have sizes and shapes suitable for use at the home or at the workplace.

The water-soluble paper consists of 99-45 weight per cent of carboxy-methyl cellulose and 1-55 weight per cent of wood pulp. Any part, for example, one end of each of the urinary test paper strips is impregnated or covered with one or more reagents and dried, whereby the spots of the reagents are formed. The amount of the reagents with which one end of the urinary test paper strips is impregnated or covered, is preferably 0.5-10 times as much as the weight of the water-soluble paper per se having the same area as the area of water soluble paper which is impregnated or covered with the reagents.

Now referring to FIG. 1, numeral 1 designates a urinary test paper strip which is made of water-soluble paper consisting of 99-45 weight per cent of carboxymethyl cellulose and 0-55 weight per cent of wood pulp. Numeral 2 designates a spot of a reagent for urinalysis with which one end of a paper strip 1 is impregnated or covered. FIG. 1(a) and FIG. 1(b) depict a spot with an impregnated area surrounding the impregnated spot; the spot of the former is square and that of the latter round. FIG. 1(c) depicts a spot with no unimpregnated area left except for the upper part thereof.

FIGS. 2 and 3 depict three spots 3, 4 and 5 of three kinds of reagents for urinalysis with which one end of said paper strip 1 is impregnated or covered. Said spots 3, 4 and 5 in FIG. 2 are placed in contact with each other; those in FIG. 3 are placed at intervals in parallel with each other. FIG. 2(a), FIG. 2(b) and FIG. 2(c) correspond to FIG. 1(a), FIG. 1(b) and FIG. 1(c) in the shape of spot, respectively. The same applies to FIG. 3(a), FIG. 3(b) and FIG. 3(c).

Figure 4B:
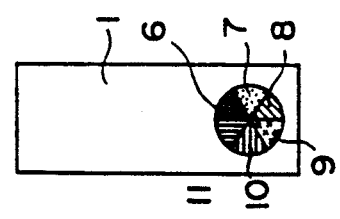
FIG. 4(a-b) shows two types of the urinary test paper strips of the present invention one end of which is impregnated or covered with five (a) or six (b) kinds of reagents, the spots of which are placed radially.
Figure 4A:
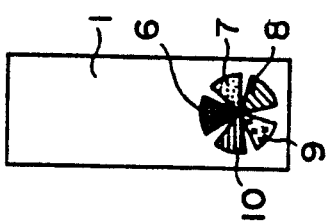

FIG. 4(a) depicts five spots 6, 7, 8, 9 and 10 of five kinds of reagents with which one end of said paper strip 1 is impregnated or covered. Said spots 6, 7, 8, 9 and 10 are placed radially at intervals. FIG. 4(b) depicts six spots 6, 7, 8, 9, 10 and 11 of six kinds of reagents with which one end of said paper strip 1 is impregnated or covered. Said spots 6, 7, 8, 9, 10 and 11 are placed radially in touch with each other.

Figure 5C:
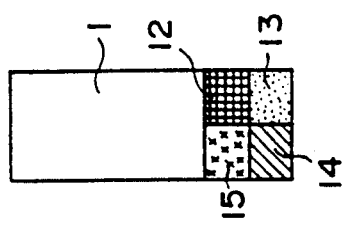
FIG. 5(a-c) shows three types of the urinary test paper strips of the present invention one end of which is impregnated or covered with four kinds of reagents, the spots of which are placed radially.
Figure 5B:
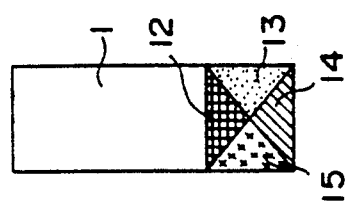
Figure 5A:
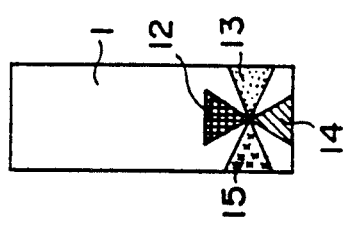

FIG. 5 depicts four spots 12, 13, 14 and 15 of four kinds of reagents with which one end of said paper strip 1 is impregnated or covered. FIG. 5(a) depicts four spots 12, 13, 14 and 15 which are placed radially at intervals, and is therefore a variation of FIG. 4(a). FIG. 5(b) and FIG. 5(c) depict four spots 12, 13, 14 and 15 which are placed radially in contact with each other and are put with no blank left except for the upper part of these spots.

FIG. 6 depicts four types of urinary test paper strips wherein the central part of one end of the paper strips is not impregnated or covered with any reagents. FIG. 6(a), FIG. 6(b), FIG. 6(c) and FIG. 6(d) correspond to FIG. 4(a), FIG. 4(b), FIG. 5(a) and FIG. 5(b), respectively.

FIG. 7, 8, 9 and 10 depict urinary test paper strips which are different in shape from those shown in FIGS. 1–6. As shown in FIGS. 6–10, one end of the paper strip 1 is rounded and this part is impregnated or covered with several reagents. A urinary test paper strip of this type is suitable in the case that two or more, particularly four or more reagents are used. As will be noted, the spots of reagents in FIG. 7(a), FIG. 7(b), FIG. 9(a) and FIG. 9(b) correspond to those in FIG. 4(a), FIG. 4(b), FIG. 6(a) and FIG. 6(b), respectively. FIG. 8(a), FIG. 8(b), FIG. 10(a) and FIG. 10(b) are variations of FIG. 7(a), FIG. 7(b), FIG. 9(a) and FIG. 9(b), respectively.

"Water-soluble paper" of the present invention means thin paper which is soluble in water and consists of 99–45 weight percent of carboxymethyl cellulose and 1–55 weight percent of wood pulp. Reagents are used for impregnating or covering a water-soluble paper strip in an amount of 0.5–10 times as much as the weight of water-soluble paper per se having the same area as the area of water-soluble paper which is impregnated or covered with said reagents.

All kinds of chemicals that are usually employed for test paper for easy urinalysis can be utilized as a reagent for urinary test paper of the present invention. Examples of such reagents are given belows.

(a) a pH-indicator such as bromoxylenol blue or bromocresol blue.

(b) a protein indicator such as a potassium salt of tetrabromophenolphthalein ethyl ester and tetrabromphenol blue.

(c) a glucose indicator such as glucose oxidase (obtained from eumycetes), peroxidase, tetrabase, guaiac resin, potassium iodide and orthotoluidine.

(d) a ketone indicator such as amino acetic acid and sodium nitroprusside.

(e) a bilirubin indicator such as 2-methyl-5-nitroaniline, sodium nitrite, 2,4-dichloroabniline and 2,6-dichlorobenzene.

(f) an occult blood indicator such as cumene hydroperoxide and orthotoluidine.

(g) a nitrite (bacteriuria) indicator such as citric acid, sodium citrate, sulfanilamide and N-(1-naphthylamino)-3-propanesulfonic acid.

(h) a urobiliogen indicator such as 3,3-dimethoxybiphenyl-4,4-diazonium tetrafluoroborate, p-dimethylaminobenzaldehyde and diazotized 4-methoxybenzene.

In accordance with the present invention, water-soluble thin paper is used which consists of 99–45 weight per cent, preferably 99–50 weight per cent, of carboxymethyl cellulose and 1–55 weight per cent, preferably 1–50 weight per cent, of wood pulp. By utilizing such paper as urinary test paper, the decomposition velocity and the dissolution velocity of said paper in water can be regulated and the strength of said paper can also be increased. In addition to these advantages, the urinary test paper of the present invention can be easily disposed of in a toilet bowl of a flush toilet or even in a urinal of a men's room after the use thereof.

Any size and shape may be chosen for the urinary test paper of the present invention as far as it is handy to carry. Therefore the urinary test paper should not be restricted to specific sizes and shapes. The amount of reagents (indicators) suitable for detection of a sign of a disease is 0.5–10 times as much as the weight of water-soluble thin paper per se having the same area as the area of water-soluble paper which is impregnated or covered with said reagents.

The urinary test paper of the present invention is exemplified more fully by the following illustrative examples. The scope of the invention is, however, not limited thereto.

EXAMPLE 1

Water-soluble paper was made from 99 weight per cent of carboxymethyl cellulose and 1 weight per cent of wood pulp. Strips of the water-soluble paper were covered with potassium iodide solution as shown in FIG. 1(a) or FIG. 1(b) and dried in order to obtain wrinary test paper strips that can detect urinary glucose the presence of which suggests a sign of diabetes and the like.

A urinary test paper strip thus obtained was used in the bathroom for urinalysis and flushed down the toilet after use. However, the toilet bowl did not get stopped up.

EXAMPLE 2

Figure 6D:
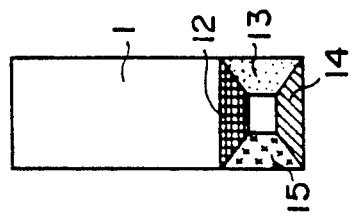
FIG. 6(a-d) shows four types of the urinary test paper strips of the present invention which are the same as those in FIG. 4 or FIG. 5 except that the central part of one end of the urinary test paper strips is not impregnated or covered with any reagents.
Figure 6C:
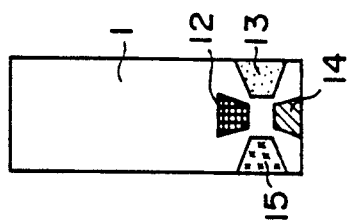
Figure 6B:
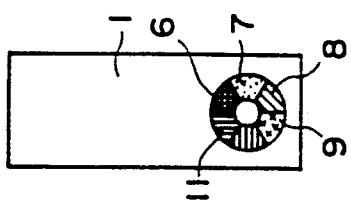
Figure 6A:
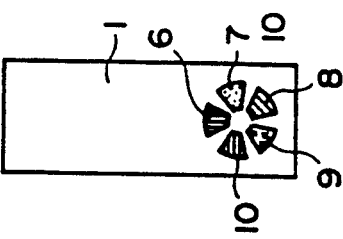

Water-soluble paper was made from 70 weight per cent of carboxymethyl cellulose and 30 weight per cent of wood pulp. Strips of the water-soluble paper were covered with peroxidase, tetrabromo-phenol blue, bromoxylenol blue and cumene hydroperoxide and dried in order to obtain urinary test paper strips that can detect signs of diabetes, diabetic nephropathy, nephritis and other diseases. The four spots of these reagents were placed radially at intervals but the central part of one end of the paper strips was not covered with these reagents, as shown in FIG. 6(c).

A urinary test paper strip thus obtained was used in a rest room for urinalysis and flushed down a urinal after use. However the urinal did not get stopped up.

EXAMPLE 3

Water-soluble paper was made from 45 weight per cent of carboxymethyl cellulose and 55 weight per cent of wood pulp. Strips of the water-soluble paper were covered with 2-methyl-5-nitroaniline, bromocresol green, p-dimethylaminobenzaldehyde, glucose-oxidase and sodium nitroprusside, and dried in order to obtain urinary test paper strips that can detect signs of liver cirrhosis, hepatitis, gout, diabetes, hepatic dysfunction, hepatic insufficiency, diabetic acidosis and other diseases. The five spots of these regents were placed at intervals in parallel with one another in the manner similar to that shown in FIG. 3(c).

A urinary test paper thus obtained was used in the bathroom for urinalysis and flushed down the toilet after use. However the toilet bowl did not get blocked.

Using the urinary test paper of the present invention, anybody can easily test his or her urine at home or in the workplace whenever necessary. In addition, the urinary test paper of the present invention can be flushed down a toilet bowl, especially even a urinal, in a flush toilet after use since the paper easily dissolves in water.

Various modifications and equivalents will be apparent to one skilled in the art and may be made in the urinary test paper of the present invention without departing from the spirit or scope thereof, and it is therefore to be understood that the invention is to be limited only by the scope of the appended claims.

What is claimed is:

1. Water-soluble urinalysis test paper comprising paper made from 99–45 weight per cent of carboxymethyl cellulose and from 1–55 weight percent of wood pulp, and coated or impregnated with at least one reagent.

2. The test paper according to claim 1 wherein the amount of said at least one reagent is from 0.5 to 10 times the weight of the water-soluble paper which is impregnated or coated with said at least one reagent.

3. The test paper according to claim 1 wherein said water-soluble paper is coated or impregnated with from one to eight types of reagents.

4. The test paper according to claim 1 wherein said water-soluble paper is in the form of strips which are rounded at one end.

5. The test paper according to claim 4 wherein said round end of said strips is coated or impregnated with at least one reagent.

6. The test paper according to claim 4 wherein said round end is coated or impregnated with at least two kinds of reagents and said at least two reagents are in contact with each other.

7. The test paper according to claim 4 wherein said round end is coated or impregnated with at least two kinds of reagents in such fashion that said reagents are located radially in contact with each other.

8. The test paper according to claim 4 wherein said round end is coated or impregnated with at least two reagents in such fashion that said reagents are located radially at intervals spaced from each other.

9. The test paper according to claim 8 wherein the central part of said round end has a blank space which is not coated or impregnated with reagent.

10. The test paper according to claim 1 wherein said water-soluble paper is in the form of strips.

11. The test paper according to claim 10 wherein an entire region of one end of said strips is coated or impregnated with one kind of reagent.

12. The test paper according to claim 10 wherein one end of said strips is covered or impregnated with one kind of reagent in such fashion that said one end has an uncoated or unimpregnated area around a spot of reagent.

13. The test paper according to claim 10 wherein one end of the strip is coated or impregnated with at least one reagent.

14. The test paper according to claim 13 wherein said one end is coated or impregnated with at least two kinds of reagents and said at least two reagents are in contact with each other.

15. The test paper according to claim 13 wherein said one end is coated or impregnated with at least two kinds of reagents in such fashion that said reagents are placed at intervals parallel to each other.

16. The test paper according to claim 13 wherein said one end is coated or impregnated with at least two kinds of reagents in such fashion that said reagents are located radially in contact with each other.

17. The test paper according to claim 13 wherein said one end is coated or impregnated with at least two reagents in such fashion that said reagents are located radially at intervals spaced from each other.

18. The test paper according to claim 17 wherein the central part of said one end has a blank space which is not coated or impregnated with reagent.

* * * * *